(12) United States Patent
Vikinsky et al.

(10) Patent No.: US 10,828,079 B2
(45) Date of Patent: Nov. 10, 2020

(54) K-WIRE ADAPTOR ASSEMBLY

(71) Applicant: PREMIA SPINE LTD., Ramat Poleg (IL)

(72) Inventors: Ofer Vikinsky, Zur-Igal (IL); Ron Sacher, Herzelia (IL)

(73) Assignee: Premia Spine Ltd., Ramat Poleg (IL)

( * ) Notice: Subject to any disclaimer, the term of this patent is extended or adjusted under 35 U.S.C. 154(b) by 310 days.

(21) Appl. No.: 15/564,006

(22) PCT Filed: Apr. 12, 2016

(86) PCT No.: PCT/IB2016/052074
§ 371 (c)(1),
(2) Date: Oct. 3, 2017

(87) PCT Pub. No.: WO2016/166662
PCT Pub. Date: Oct. 20, 2016

(65) Prior Publication Data
US 2018/0132920 A1    May 17, 2018

Related U.S. Application Data

(60) Provisional application No. 62/146,318, filed on Apr. 12, 2015.

(51) Int. Cl.
*A61B 17/58* (2006.01)
*A61B 17/88* (2006.01)
*A61B 17/70* (2006.01)

(52) U.S. Cl.
CPC ...... *A61B 17/8897* (2013.01); *A61B 17/7082* (2013.01); *A61B 17/888* (2013.01); *A61B 17/8875* (2013.01); *A61B 17/8872* (2013.01)

(58) Field of Classification Search
CPC ............ A61B 17/8897; A61B 17/7082; A61B 17/888; A61B 17/8872; A61B 2017/90
(Continued)

(56) References Cited

U.S. PATENT DOCUMENTS 7,326,203 B2 * 2/2008 Papineau ......... A61B 17/32002
606/104
2006/0248988 A1 * 11/2006 Bennett ............. A61B 17/1624
81/62

(Continued)

OTHER PUBLICATIONS

PCT Search Report and Written Opinion PCT/IB2016/052074, dated Aug. 25, 2016.

*Primary Examiner* — Jessica Weiss
(74) *Attorney, Agent, or Firm* — Dekel Pant Ltd.; David Klein

(57) ABSTRACT

A surgical tool adaptor includes a distal interface member and a handle. The distal interface member includes a connecting element for connecting to a surgical tool. A K-wire connector is disposed in a central passageway for receiving therethrough a K-wire. The K-wire connector includes a locking element for locking the K-wire. A clutch mechanism is operatively connected to the distal interface member and to the K-wire connector, wherein in a first orientation of the clutch mechanism, the distal interface member and the K-wire connector move together, and in a second orientation of the clutch mechanism, the distal interface member is declutched from the K-wire connector, so that in the first orientation movement of the handle moves the distal interface member and the K-wire connector together, and in the second orientation the distal interface member and the K-wire connector move independently of each other.

12 Claims, 5 Drawing Sheets

(58) Field of Classification Search
USPC ...................................... 606/103–104, 96–98
See application file for complete search history.

(56) References Cited

U.S. PATENT DOCUMENTS

| | | |
|---|---|---|
| 2009/0228013 A1 | 9/2009 | Bourque |
| 2009/0254094 A1* | 10/2009 | Knapp ............... A61B 17/1637 606/96 |
| 2012/0004665 A1 | 1/2012 | Defossez |
| 2014/0276892 A1* | 9/2014 | Pakzaban ........... A61B 17/8875 606/104 |
| 2014/0276894 A1* | 9/2014 | Ramsay ............. A61B 17/7076 606/104 |

* cited by examiner

K-WIRE ADAPTOR ASSEMBLY

FIELD OF THE INVENTION

The present invention relates generally to methods and apparatus for controlled placement of surgical devices over a Kirschner wire (K-wire), such as but not limited to, screwdrivers, taps, bores, awls, probes, jamshidi needles, and others.

BACKGROUND OF THE INVENTION

Medical procedures involving the vertebrae are normally complicated because of the preciseness and accuracy required to avoid both neural damage and injury to major blood vessels. For example, some medical procedure require placing an anchor of some sort (e.g., screw) into a specific place in the vertebrae. Misalignment or other incorrect placement of the screw can result in injury or failure in the connection between the bone and hardware. These surgeries sometimes require penetration of the hard cortical bone of the vertebra and traversal of the softer cancellous bone lying thereunder. A large force is normally required by the surgeon to penetrate the cortical bone. Once the cortical bone is penetrated, extreme care must then be taken to avoid rapidly penetrating through all of the cancellous bone. There is also the danger of rapidly passing through the cancellous bone and then through the cortical bone on the other side of the vertebra. This can result in injury or damage to the spinal cord and/or other organs or blood vessels located adjacent the spine.

For example, in certain surgical procedures, a K-wire or similar guide wire (the terms being used interchangeably throughout) is used in combination with a cannulated surgical tool, such as a screwdriver, tap, bore, awl, probe, or jamshidi needle, to name some. The K-wire is positioned through the pedicle and into the vertebral body to indicate or establish the position of subsequent screw placement. Once the proper positioning of the K-wire is confirmed by X-rays, the screw connected to the screwdriver is guided over the K-wire through the lumen (cannula) of the surgical tool and penetrates into the bone, which if not done properly can injure the patient, particularly if the K-wire encounters certain sensitive tissues. The procedures often require the use of force which can cause an otherwise properly positioned K-wire to move forward into the surgical site, which if excessive can move into contact where contact is to be avoided.

Thus, controlling the position of the K-wire sharp tip is critical for the patient safety. In a normal screw placement over a K-wire, the K-wire is placed to the desired depth, and then the screw is advanced over the K-wire. The surgeon must make sure the tip of the K-wire is not pushed further distally towards the anterior cortex of the vertebral body. If the K-wire tip were to puncture through the vertebra it could damage major blood vessels and cause major bleeding.

SUMMARY OF THE INVENTION

The present invention seeks to provide an improved device for controlled placement of surgical devices over a K-wire, as described more in detail hereinbelow.

The term K-wire throughout the specification and claims encompasses any slender, elongated piece with a tip used for entering bone, such as a K-wire or Steinmann pin.

In brief, the device enables inserting a K-wire through a lumen of a cannulated surgical tool. In the case of a screwdriver, for example, the K-wire also passes through the lumen of the screw. The device is easily used to position the K-wire so it protrudes a little bit (e.g., a few mm) beyond the distal tip of the screw or surgical tool. The device is then used to lock the K-wire with respect to the screw or tool. The device is adjustable so that its proximal end can be flush with the proximal end of the K-wire, so that the surgeon can hammer or otherwise apply force on the proximal end of the device in order to advance the K-wire and screw or tool together. The K-wire breaches the cortical bone (or other spinal structure which the surgeon wishes to breach) and brings the tip of the cannulated screw or tool to the bone surface. From there, the surgeon can screw in the pedicle screw or advance the tool without concern for slipping. Without the device, the screw or tool can slip at the point of entry. The tip of the k-wire also ensures that the entry point is not lost during screw angulation, and facilitates finding or changing entry points The invention saves time and effort to insert screw or other surgical tools.

There is thus provided in accordance with an embodiment of the present invention an assembly including a surgical tool adaptor including a distal interface member and a handle, the distal interface member including a connecting element for connecting to a surgical tool, a central passageway being formed through the distal interface member and the handle, a K-wire connector disposed in the central passageway for receiving therethrough a K-wire, the K-wire connector including a locking element for locking the K-wire, and a clutch mechanism operatively connected to the distal interface member and to the K-wire connector, wherein in a first orientation of the clutch mechanism, the distal interface member and the K-wire connector move together, and in a second orientation of the clutch mechanism, the distal interface member is declutched from the K-wire connector, so that in the first orientation movement of the handle moves the distal interface member and the K-wire connector together, and in the second orientation the distal interface member and the K-wire connector move independently of each other.

In accordance with an embodiment of the present invention, in the second orientation, a first movement of the handle moves the K-wire connector while the distal interface member remains stationary.

In accordance with an embodiment of the present invention, in the second orientation, a second movement of the handle moves the distal interface member while the K-wire connector remains stationary.

In accordance with an embodiment of the present invention, in the second orientation, a third movement of the handle moves the distal interface member in one direction and moves the K-wire connector in a different direction.

In accordance with an embodiment of the present invention the clutch mechanism is movably connected to the handle.

In accordance with an embodiment of the present invention (FIGS. 1A, 1B and 2) the clutch mechanism includes a first ratchet mechanism operatively connected between the distal interface member and the handle, which in a first direction causes the distal interface member and the handle to move together and in a second direction declutches the distal interface member from the K-wire connector, so that in the first direction movement of the handle moves the distal interface member and the K-wire connector together, and in the second direction movement of the handle moves the distal interface member without moving the K-wire connector. The assembly may further include an adjustment knob operative to move the K-wire connector independently of the first ratchet mechanism.

The assembly may further include a second ratchet mechanism operatively connected between the adjustment knob and the handle, which in the first direction declutches the K-wire connector with respect to the adjustment knob, and in the second direction causes the adjustment knob and the K-wire connector to move together, so that in the second direction movement of the handle moves the adjustment knob and the K-wire connector together.

In accordance with another embodiment of the present invention (FIGS. 3A-3G) the clutch mechanism includes a ratchet assembly that includes a mode transition element and a ratchet member formed with ratchet teeth arranged to engage teeth formed on the distal interface member, and wherein the handle engages the mode transition element, so that turning the handle causes axial movement of the mode transition element.

In accordance with an embodiment of the present invention (FIGS. 4A-4D) the clutch mechanism includes an auxiliary handle connected to the distal interface member, and wherein the first-mentioned handle is connected to the K-wire connector and the first-mentioned handle and the auxiliary handle are coaxial.

In accordance with an embodiment of the present invention a K-wire is disposed through the central passageway and locked to the K-wire connector.

In accordance with an embodiment of the present invention a surgical tool is connected to the connecting element. The surgical tool may include a screw, a screwdriver, a tap, a bore, an awl, a probe, or a jamshidi needle.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1A:
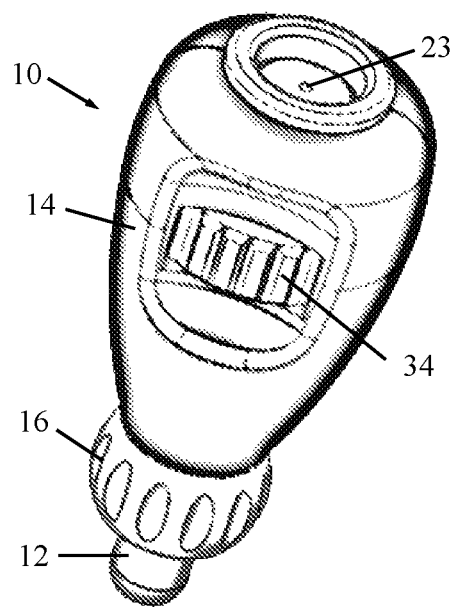
FIGS. 1A and 1B are simplified perspective views of a surgical tool adaptor, constructed and operative in accordance with an embodiment of the present invention.
Figure 1B:
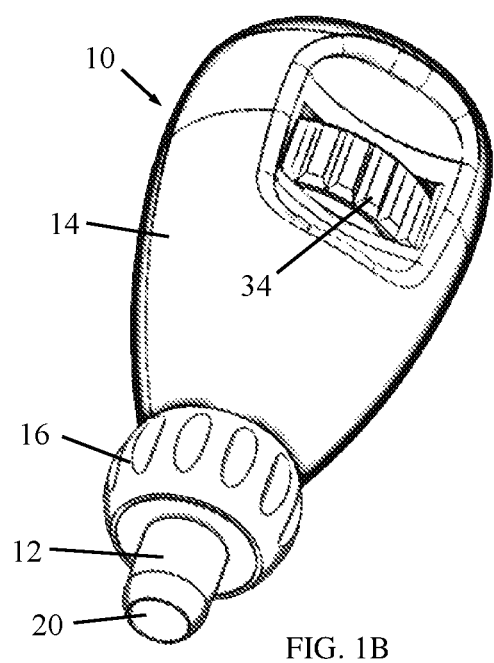
Figure 2:
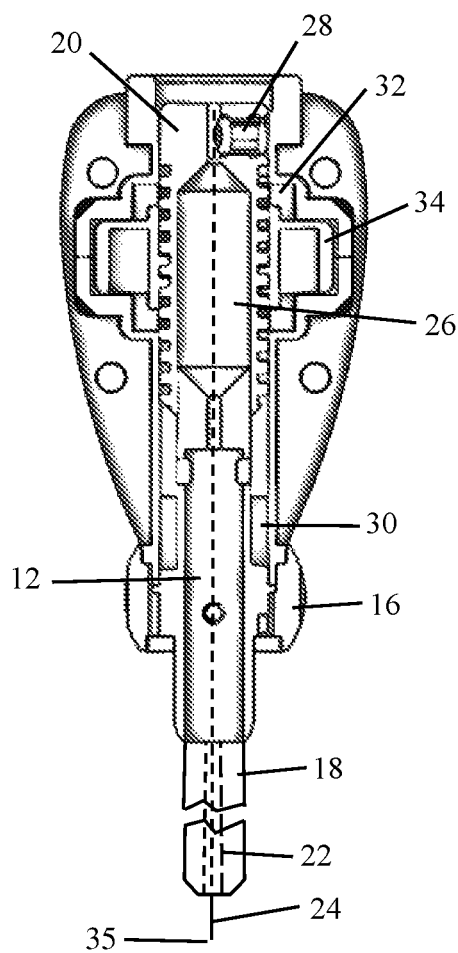
FIG. 2 is a simplified cutaway-view illustration of the surgical tool adaptor.

Reference is now made to FIGS. 1A, 1B and 2, which illustrate a surgical tool adaptor 10, constructed and operative in accordance with a non-limiting embodiment of the present invention.

Surgical tool adaptor 10 includes a distal interface member 12 and a handle 14. Distal interface member 12 includes a connecting element 16 for connecting to a surgical tool 18 (FIG. 2). (For example, distal interface member 12 may be a screwdriver connector for connecting to a screwdriver.) The connecting element 16 may include, without limitation, a locking knob with an internally threaded bore or a male or female connector for connection with the surgical tool 18. Surgical tool adaptor 10 is formed with a central passageway or lumen 20 formed through distal interface member 12 and handle 14.

The surgical tool 18 may include, without limitation, a screw, a screwdriver, a tap, a bore, an awl, a probe, or a jamshidi needle and the like. Surgical tool 18 is formed with a lumen 22. Two or more surgical tools may be connected to each other, such as a screwdriver connected to a pedicle screw.

A K-wire 24 (FIG. 2) passes through central passageway 20 of surgical tool adaptor 10 distally through distal interface member 12 into lumen 22 of surgical tool 18 and distally out the distal tip of surgical tool 18 (the distal end of K-wire 24 is seen in FIG. 2). An entrance hole 23 (FIG. 1A) is formed at the top of handle 14 for introducing the K-wire 24 into the handle 14. A K-wire connector 26 is disposed in handle 14. K-wire 24 passes through K-wire connector 26 and is locked in place by a locking element 28 (such as, but not limited to, a set screw).

In summary to this point, surgical tool adaptor 10 can be fixed on surgical tool 18 by locking distal interface member 12 onto surgical tool 18 with connecting element 16. The K-wire 24 passes through the lumens of surgical tool adaptor 10 and surgical tool 18. The K-wire 24 is locked in place with locking element 28.

The present invention provides a K-wire adaptor control system for controlling the amount the sharp tip of K-wire 24 protrudes from the distal end of surgical tool 18, as is now explained.

The K-wire adaptor control system includes first and second ratchet mechanisms 30 and 32, respectively (FIG. 2). The term "ratchet" encompasses not only mechanisms with a pawl and teeth, but also any kind of mechanism that permits motion (rotation or linear motion or a combination of such motions) in one direction only (e.g., only clockwise or only counterclockwise). Thus, the term ratchet as used herein not only encompasses a ratchet but also one-way bearings, for example. The K-wire adaptor control system is a type of clutch mechanism.

The first and second ratchet mechanisms 30 and 32 divide the use of the surgical tool 18 into two distinct and separately controlled actions. Rotation of handle 14 in a first direction (e.g., clockwise) turns surgical tool 18 in the first direction (e.g., so as to turn a screwdriver to threadingly advance a screw into bone). Rotation of handle 14 in a second direction, opposite to the first direction (e.g., counterclockwise) moves the tip of K-wire 24 proximally (backwards) while the surgical tool 18 is held stationary in place.

The first ratchet mechanism 30 is operatively connected between distal interface member 12 and handle 14. The second ratchet mechanism 32 is operatively connected between a K-wire adjustment knob 34 and handle 14. The first and second ratchet mechanisms 30 and 32 work in opposite directions: when the first ratchet mechanism 30 allows rotation the second ratchet mechanism 32 blocks rotation and vice versa. The K-wire adjustment knob 34 and handle 14 may be threaded the same way, or alternatively, may be threaded in different directions (one right-handed threads and the other left-handed threads).

When rotating handle 14 in the first direction (e.g., clockwise, such as to advance a screw), the first ratchet mechanism 30 does not freely move and instead transfers the moment from handle 14, thereby turning surgical tool 18 in the first direction (e.g., so as to turn a screwdriver to threadingly advance a screw into bone). The first ratchet mechanism 30 locks distal interface member 12 and handle 14 together, which means the K-wire advances together with the surgical tool 18. The protrusion of the top of the K-wire remains constant. The second ratchet mechanism 32 turns freely in the first direction, meaning K-wire connector 26 is declutched with respect to adjustment knob 34.

Optionally, a third ratchet (not shown) may be provided that allows axial movement between K-wire connector 26 and K-wire connector 12 when turning K-wire adjustment knob 34 and release the lock when rotating the handle 14 in the second direction so to allow the K-wire connector 26 to remain stationary while the handle 14 is rotated with the knob 34.

When rotating handle 14 in the second direction (e.g., counterclockwise), first ratchet mechanism 30 declutches distal interface member 12 from K-wire connector 26, which means the K-wire is now free to move with respect to surgical tool 18, thus allowing adjustment of the K-wire tip protrusion.

In the second direction, the second ratchet mechanism 32 fixes handle 14 with respect to adjustment knob 34. When rotating handle 14 in the second direction, adjustment knob 34 rotates together with the handle 14 and this causes K-wire connector 26 to move proximally with respect to distal interface member 12, thus moving the K-wire tip proximally (backwards).

The second ratchet mechanism 32 allows rotation of adjustment knob 34 individually relative to handle 14 for the preliminary adjustment of the K-wire length relative to the distal tip of the tool 18. The knob 34 allows only forward (distal) adjustment. As mentioned before, backing the K-wire tip relative to the tool tip is performed by rotating the handle 14 in the second direction (e.g., counterclockwise).

The surgical tool adaptor 10 is adjustable so that its proximal end (entrance hole 23 seen in FIG. 1A) can be flush with the proximal end of the K-wire, so that the surgeon can hammer or otherwise apply force on the proximal end of the surgical tool adaptor 10 in order to advance the K-wire and screw or tool together.

In another embodiment of the invention, a force sensor 35, such as but not limited to, a load cell, strain gauge or impedance sensor, is mounted on the K-wire 24 (FIG. 2). The force sensor 35 can sense and alert changes in load applied on the tip of wire 24. For example, when the wire 24 touches a cortical bone, bending of axial forces are sensed by force sensor 35, which sends a signal to a processor (not shown) that alerts the surgeon that the screw is about to breach the pedicle or vertebral body. Alternatively, the system can detect and alert when the load is reduced, for example, if the tip has crossed the pedicle into the cancellous bone.

Reference is now made to FIGS. 3A-3G, which illustrate a surgical tool adaptor 40, constructed and operative in accordance with a non-limiting embodiment of the present invention.

Figure 3A:
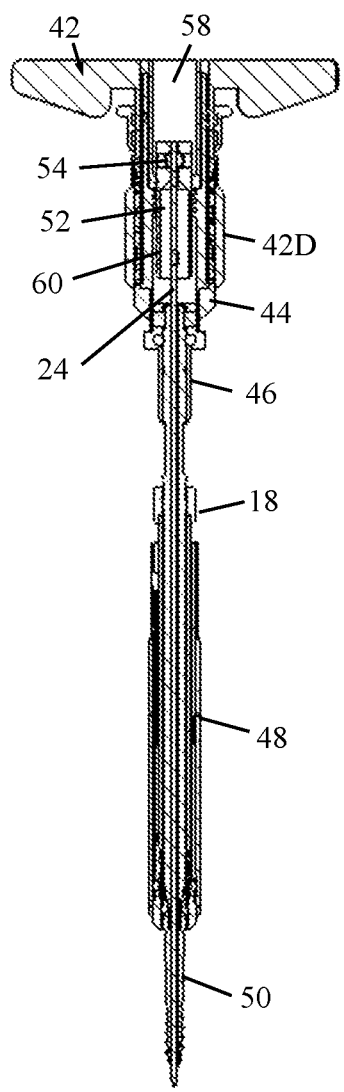
FIG. 3A is a simplified sectional illustration of a surgical tool adaptor, constructed and operative in accordance with another non-limiting embodiment of the present invention.
Figure 3B:
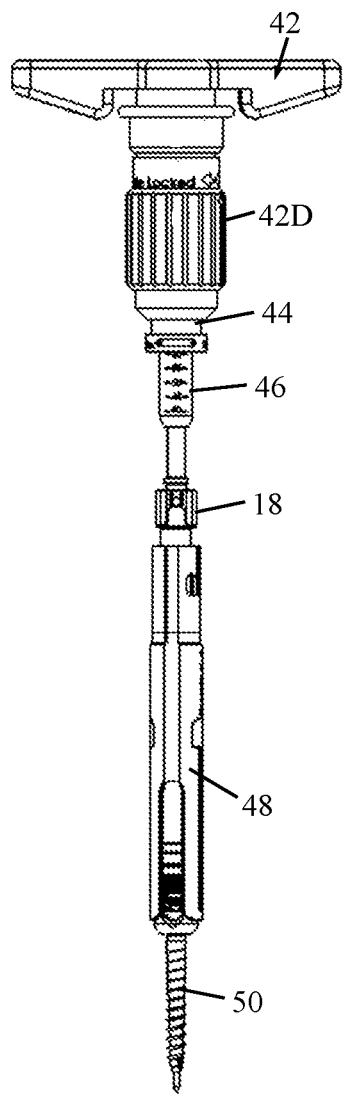
FIG. 3B is a simplified pictorial illustration of the surgical tool adaptor of FIG. 3A.
Figure 3C:
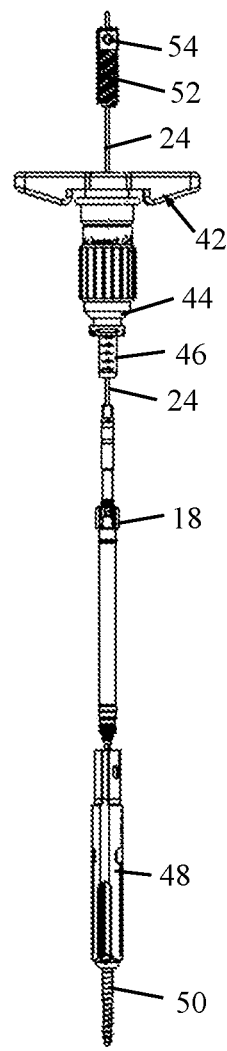
FIG. 3C is a simplified pictorial illustration of the surgical tool adaptor, with some of the parts separated so as to show a K-wire that passes through a K-wire adaptor screw.
Figures 3D, 3E:
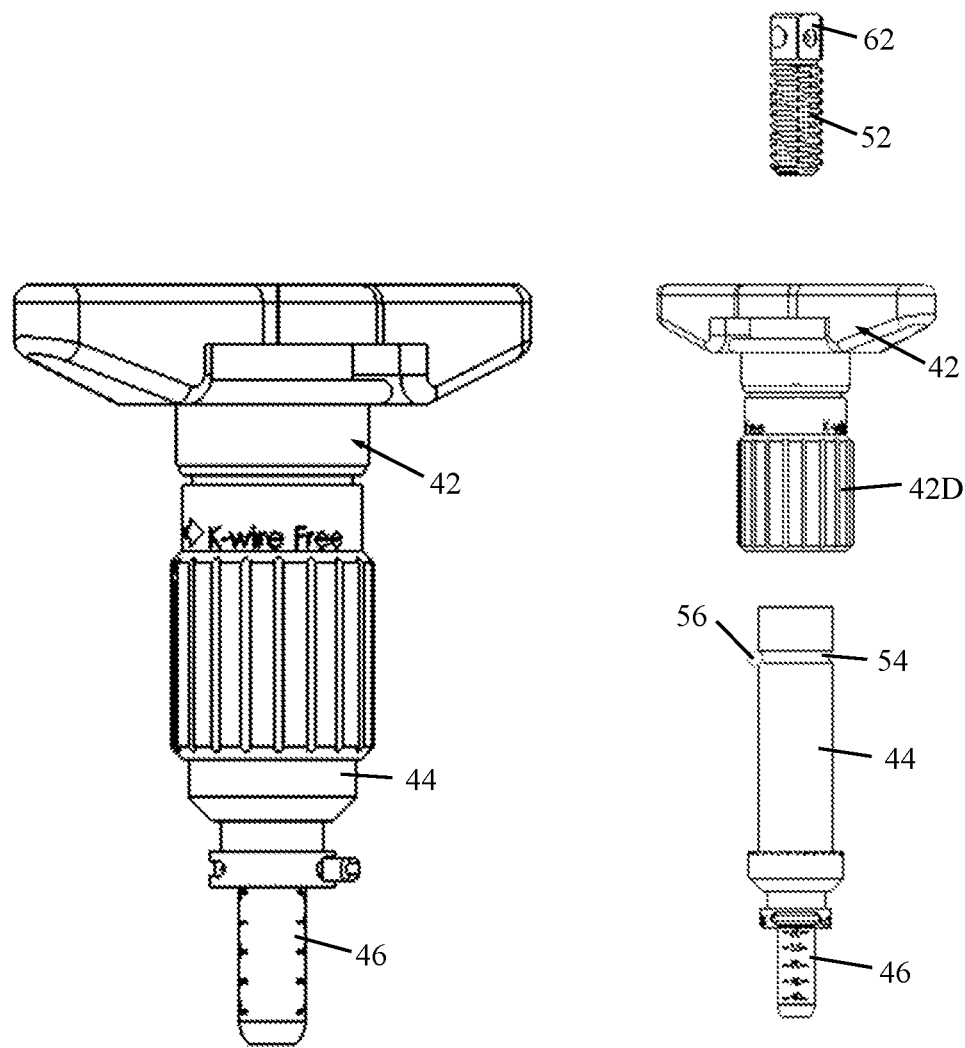
FIGS. 3D and 3E are simplified pictorial illustrations of a handle of the surgical tool adaptor of FIG. 3A mounted and dismounted from a distal interface member, respectively.
Figures 3F, 3G:
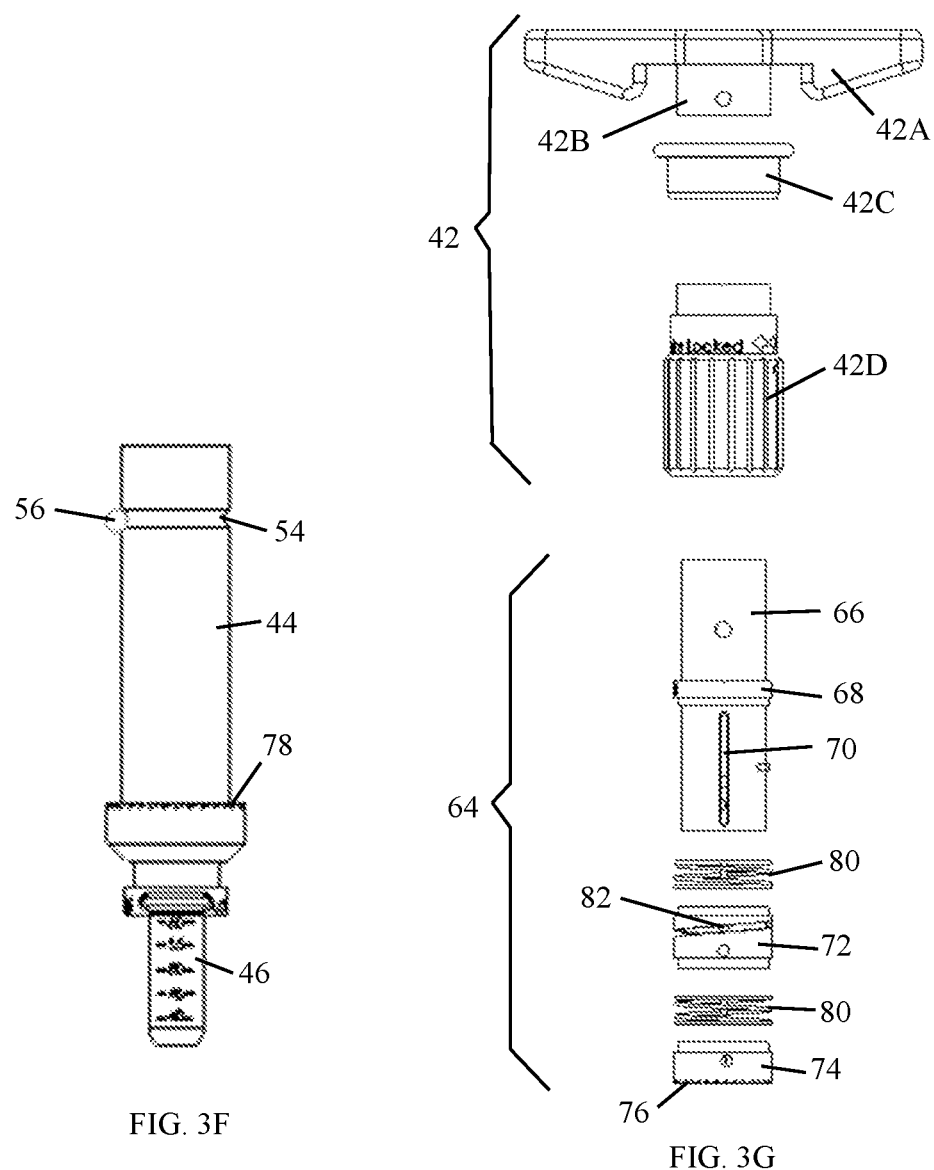
FIG. 3F is a simplified pictorial illustration of the distal interface member.
FIG. 3G is a simplified exploded illustration of the handle and the ratchet assembly of the surgical tool adaptor of FIG. 3A.
Figure 4A:
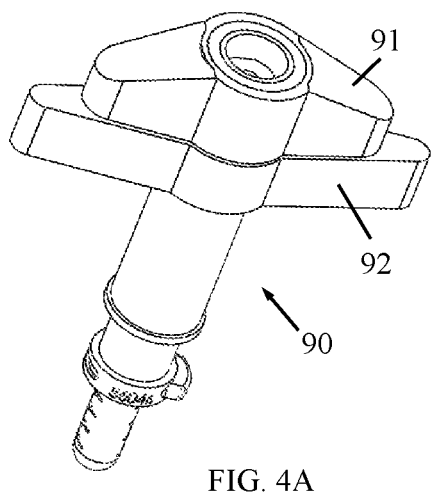
FIGS. 4A and 4B are simplified pictorial illustrations of a surgical tool adaptor, constructed and operative in accordance with another non-limiting embodiment of the present invention, with two handles at different rotational orientations with respect to each other.
Figure 4B:
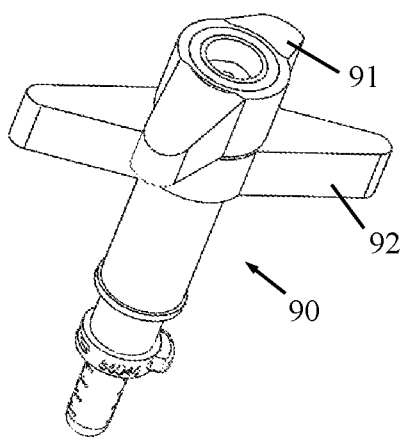
Figure 4C:
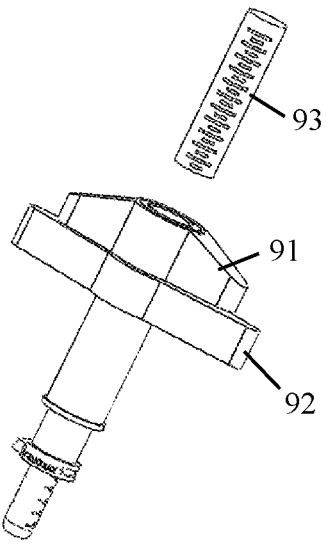
FIGS. 4C and 4D are simplified pictorial and cutaway illustrations, respectively, of the surgical tool adaptor of FIG. 4A with an additional scale insert mounted in the adaptor.
Figure 4D:
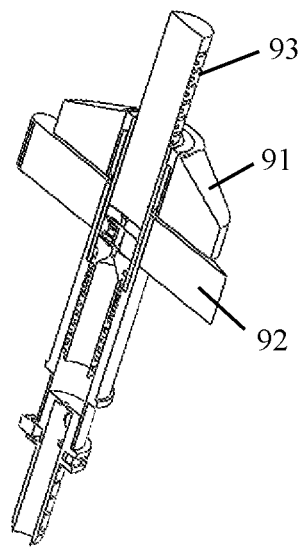

Surgical tool adaptor 40 includes a handle 42, which as seen in FIG. 3G, may include winged protrusions 42A for easy turning, a hub 42B that fits through a bushing 42C that affixes to a barrel 42D. Handle 42 is rotatingly mounted on a distal interface member 44, which similarly to the previous embodiment, includes a connecting element 46 for connecting to a surgical tool 18, such as but not limited to, a screwdriver that can pass through a tower 48 for screwing a pedicle screw 50 (FIGS. 3A-3C). Alternatively, as before, surgical tool 18 may include, without limitation, a screw, a tap, a bore, an awl, a probe, or a jamshidi needle and the like.

A K-wire 24 (FIGS. 3A-3C) passes through a central passageway of surgical tool adaptor 40 distally through distal interface member 44 and connecting element 46, and distally out the distal tip of surgical tool 18. K-wire 24 passes through a K-wire adjustment screw 52 and may be locked in place by a locking element 54 (such as, but not limited to, a set screw in FIGS. 3A and 3C). K-wire adjustment screw 52 serves as a K-wire connector.

As seen in FIG. 3E, the distal interface member 44 may be formed with an annular groove 54, which is provided with a ball 56. Handle 42 may be connected to distal interface member 44 by forcing the handle over the groove 54 so that the ball 56 fits into an annular recess (not shown) inside the handle 42. In this manner, the handle 42 is constrained to rotate about distal interface member 44 (smooth rotation due to the ball 56) and the handle 42 cannot be pulled out axially from distal interface member 44.

As seen in FIG. 3A, the K-wire adjustment screw 52 is inserted through a lumen 58 in the handle 42 until it threadingly mates with internal threads 60 formed in the handle 42. As seen in FIG. 3E, K-wire adjustment screw 52 has anti-turning structure 62, such as flats formed at the top of the screw 52. These flats sit in a corresponding square aperture (not shown) in handle 42 so that screw 52 can only turn together with handle 42 and cannot turn independently of handle 42.

K-wire adjustment screw 52 preferably has the same screw pitch as the pedicle screw 50 to ensure synchronized motion with the screw 50.

As seen in FIG. 3G, handle 42 is connected to a ratchet assembly 64 (type of clutch mechanism), which may include a sleeve member 66 formed with a stop 68 and a guide groove 70. Ratchet assembly 64 further includes a mode transition element 72 and a ratchet member 74, formed with ratchet teeth 76 on a bottom surface thereof that can engage teeth 78 formed on an upwardly facing surface of distal interface member 44 (FIG. 3F). The mode transition element 72 may be biased against sleeve member 66 and against ratchet member 74 by biasing devices 80, such as coil springs. Handle 42 may have an internal pin (not shown) that engages a helical groove 82 formed on mode transition element 72, so that turning handle 42 causes axial movement of mode transition element 72. The mode transition element 72 and the ratchet member 74 are locked for rotation relative to sleeve member 66 with a pin that fits in groove 70. This connection permits axial movement and prevents rotation.

In operation, the adjustment of K-wire 24 is achieved by rotating handle 42 relative to distal interface member 44.

The surgical tool adaptor 40 has three working modes:
1. Adjustment of K-wire protrusion from the distal tip of the screw 50 (or whatever tool or item is connected to adaptor 40)
2. Advancement or retraction of the screw 50 and K-wire 24 together as one unit 3. Advancement of the screw 50 while retracting the K-wire 24 to enable inserting the screw 50 while securing the position of the sharp K-wire tip The selection of the operational mode depends upon the position of mode transition element 72, which can be moved to three different operational positions by handle 42. In a first position, the mode transition element 72 is completely disengaged from distal interface member 44 (that is, teeth 76 and 78 do not mesh). In the first position, K-wire 24 is free to move with respect to screw 50 (operational mode one, for adjusting the amount of K-wire protrusion from the distal tip of the screw 50).

In the second position, turning handle 42 (e.g., clockwise) brings the handle 42 against stop 68 and locks K-wire 24 to move together with screw 50 (operational mode two).

The third position is intermediate the first and second positions. In the third position, the K-wire 24 can advance in clockwise rotation together with screw 50 by ratchet engagement of teeth 74 and 76; however, counterclockwise rotation causes the K-wire 24 to move freely and independently of screw 50 (so that K-wire 24 can be moved back proximally without affecting the position of screw 50—operational mode three).

Reference is now made to FIGS. 4A-4D, which illustrate a surgical tool adaptor 90, constructed and operative in accordance with a non-limiting embodiment of the present invention.

Surgical tool adaptor 90 may be constructed similar to surgical tool adaptor 40, except that surgical tool adaptor 90 does not have a ratchet assembly, Instead, surgical tool adaptor 90 includes first and second handles 91 and 92. The first handle 90 is arranged to rotate the K-wire adjustment screw, while the second handle 92 is arranged to rotate the pedicle screw. Accordingly, rotation of the first handle 91, while the second handle 92 remains stationary, moves the K-wire but not the screw (operational mode one, for adjusting the amount of K-wire protrusion from the distal tip of the screw 50). Rotation of the first handle 91 together with the second handle 92 moves the K-wire together with the screw (operational mode two). Thus, when the surgeon holds both handles he/she advances or retracts the screw with the K-wire into or out of the pedicle. When the surgeon rotates only the second handle 92, he/she inserts the screw over the K-wire. The first handle 91 may be used to verify that the K-wire is not pushed by the screw further into the vertebral body. The tip of the k-wire is anchored in the bone and so rotation of the screw when guided over the k-wire does not apply moment that rotates the first handle 91. The two handles form a type of clutch mechanism.

An additional scale insert 93 can be mounted in the adaptor 90 to provide an indication of relative movement.

In another option surgical tool adaptor 90 does have a ratchet assembly, which forms a ratchet connection between handles 91 and 92. In this option, in a first rotational direction (e.g., clockwise), handles 91 and 92 rotate together, whereas in a second rotational direction (e.g., counterclockwise), only first handle 91 (the K-wire handle) can rotate (e.g., to retract the K-wire to its original position), while the second handle 92 does not rotate. The resolution of the ratchet may be, for example, one half turn.

What is claimed is:

1. An assembly comprising:
    a surgical tool adaptor comprising a distal interface member and a handle, said distal interface member comprising a connecting element for connecting to a surgical tool, a central passageway being formed through said distal interface member and said handle;
    a K-wire connector disposed in said central passageway for receiving therethrough a K-wire, said K-wire connector comprising a screw-thread capturing element for capturing the K-wire; and
    a clutch mechanism operatively connected to said distal interface member and to said K-wire connector, wherein in a first orientation of said clutch mechanism, said distal interface member and said K-wire connector move together, and in a second orientation of said clutch mechanism, said distal interface member is declutched from said K-wire connector, such that in the first orientation movement of said handle moves said distal interface member and said K-wire connector together, and in the second orientation said distal interface member and said K-wire connector move independently of each other.

2. The assembly according to claim 1, wherein in the second orientation, a movement of said handle moves said K-wire connector while said distal interface member remains stationary.

3. The assembly according to claim 1, wherein in the second orientation, a movement of said handle moves said distal interface member while said K-wire connector remains stationary.

4. The assembly according to claim 1, wherein in the second orientation, a movement of said handle moves said distal interface member in one direction and moves said K-wire connector in a different direction.

5. The assembly according to claim 1, wherein said clutch mechanism is movably connected to said handle.

6. The assembly according to claim 1, wherein said clutch mechanism comprises a first ratchet mechanism operatively connected between said distal interface member and said handle, wherein in a first direction of movement of said handle, said first ratchet mechanism causes said distal interface member and said handle to move together, and in a second direction of movement of said handle, said first ratchet mechanism declutches said distal interface member from said K-wire connector, such that in the first direction, movement of said handle moves said distal interface member and said K-wire connector together, and in the second direction, movement of said handle moves said distal interface member without moving said K-wire connector.

7. The assembly according to claim 6, further comprising an adjustment knob operative to move said K-wire connector independently of said first ratchet mechanism.

8. The assembly according to claim 7, further comprising a second ratchet mechanism operatively connected between said adjustment knob and said handle, wherein in the first direction of movement of said handle, said second ratchet mechanism declutches said K-wire connector with respect to said adjustment knob, and in the second direction of movement of said handle, said second ratchet mechanism causes said adjustment knob and said K-wire connector to move together, such that in the second direction, movement of said handle moves said adjustment knob and said K-wire connector together.

9. The assembly according to claim 1, wherein said clutch mechanism comprises a ratchet assembly that comprises a mode transition element and a ratchet member formed with ratchet teeth arranged to engage teeth formed on said distal interface member, and wherein said handle engages said mode transition element; such that turning said handle causes axial movement of said mode transition element.

10. The assembly according to claim 1, wherein said clutch mechanism comprises an auxiliary handle connected to said distal interface member, and wherein said handle of said surgical tool adaptor is connected to said K-wire connector and said handle of said surgical tool adaptor and said auxiliary handle are coaxial.

11. The assembly according to claim 1, further comprising a K-wire disposed through said central passageway and coupled to said K-wire connector.

12. The assembly according to claim 1, further comprising a surgical tool connected to said connecting element.

* * * * *